United States Patent
Kang (10) Patent No.: US 7,883,900 B2
(45) Date of Patent: Feb. 8, 2011

(54) ENHANCEMENT OF SENSITIVITY OF FLUOROPHORE MEDIATED BIOSENSING AND BIOIMAGING

(75) Inventor: Kyung A. Kang, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 0 days.

(21) Appl. No.: 11/394,290

(22) Filed: Mar. 30, 2006

(65) Prior Publication Data

US 2008/0160637 A1    Jul. 3, 2008

Related U.S. Application Data

(62) Division of application No. 11/190,199, filed on Jul. 26, 2005.

(60) Provisional application No. 60/590,992, filed on Jul. 26, 2004.

(51) Int. Cl.
  G01N 33/00    (2006.01)
  G01N 33/48    (2006.01)
  G01N 33/487   (2006.01)
  G01N 33/50    (2006.01)
  G01N 33/52    (2006.01)
  G01N 33/53    (2006.01)
  G01N 33/532   (2006.01)
  G01N 21/00    (2006.01)
  G01N 21/63    (2006.01)
  G01N 21/64    (2006.01)
  G01N 21/76    (2006.01)

(52) U.S. Cl. ............ 436/172; 436/164; 435/7.1; 435/7.94; 435/287.2; 435/288.7; 422/68.1; 422/82.05; 422/82.06; 422/82.07; 422/82.08; 977/773; 977/777; 977/904

(58) Field of Classification Search ............ 435/7.1, 435/7.94; 436/172
See application file for complete search history.

(56) References Cited

U.S. PATENT DOCUMENTS 4,622,291 A        11/1986   Picciolo et al.
5,262,526 A  *     11/1993   Sasamoto et al. ......... 534/551

(Continued)

FOREIGN PATENT DOCUMENTS

JP    2004-177348 A    6/2004

(Continued)

OTHER PUBLICATIONS

Frankewich, Raymond P., et al. *Evaluation of the Relative Effectiveness of Different Water-Soluble B-Cyclodextrin Media to Function as Fluorescence Enhancement Agents.* Anal. Chem. 1991, 63, 2924-2933.

(Continued)

*Primary Examiner*—Unsu Jung
(74) *Attorney, Agent, or Firm*—Greer, Burns & Crain Ltd.

(57) ABSTRACT

A method of enhancing fluorescence emission in a fluorophore-mediated sensing, biosensing, imaging, and bioimaging. An example of biosensing is a fluorophore-mediated sandwich immunoassay with a 1° monoclonal antibody against a target analyte and a fluorophore-linked 2° monoclonal antibody, exposing the immunoassay to an enhancing agent, applying excitation light to the immunoassay, and measuring an emission signal from the immunoassay.

10 Claims, 8 Drawing Sheets

U.S. PATENT DOCUMENTS

| | | | |
|---|---|---|---|
| 5,316,909 A | | 5/1994 | Xu |
| 5,373,093 A | | 12/1994 | Vallarino et al. |
| 5,375,606 A | * | 12/1994 | Slezak et al. ............... 600/504 |
| 5,538,857 A | | 7/1996 | Rosenthal et al. |
| 5,726,026 A | | 3/1998 | Wilding et al. |
| 6,200,762 B1 | | 3/2001 | Zlokarnik et al. |
| 6,358,526 B1 | * | 3/2002 | Mergens et al. ............ 424/464 |
| 2001/0038849 A1 | * | 11/2001 | Dang ........................ 424/428 |

FOREIGN PATENT DOCUMENTS

WO     WO 2004/046100 A2     6/2004

OTHER PUBLICATIONS

Rodriguez, Javier, et al. *AM1 Study of the Ground and Excited State Potential Energy Surfaces of Symmetric Carbocyanines.* J. Phys. Chem. A 1997, 101, 6998-7006.

Ruckebusch, Cyril, et al. *Hydrolysis of haemoglobin surveyed by infrared spectroscopy: I. Solvent effect on the secondary structure of haemoglobin.* Journal of Molecular Structure 478 (1999) 185-191.

Gruber, Hermann J., et al. *Anomalous Fluorescence Enhancement of Cy3 and Cy3.5 versus Anomalous Fluorescence Loss of Cy5 and Cy7 upon Covalent Linking to IgG and Noncovalent Binding to Avidin.* Bioconjugate Chem. 2000, 696-704. vol. 11.

De, Swati, et al *Enhanced fluorescence of triphenylmethane dyes in aqueous surfactant solutions at supramicellar concentrations—effect of added electrolyte.* Spectrochimica Acta Part A 58(2002) 2547-25555.

Dubertret, Benoit, et al. *Single-mismatch detection using gold-quenched fluorescent oligonucleotides.* 2001 Nature Publishing Group http://biotech.nature.com Nature Biotech., vol. 19, pp. 365-370.

Oswald, Bernhard, et al. *Novel Diode Laser-compatible Fluorophores and Their Application to Single Molecule Detection, Protein Labeling and Fluorescence Resonance Energy Transfer Immunoassay.* Photochemistry and Photobiology, 2001, 74(2): 237-245.

Anderson, George P., et al. *Improved fluoroimmunoassays using the dye Alexa Fluor 647 with the RAPTOR, a fiber optic biosensor* Journal of Immunological Methods 271 (2002) 17-24.

Kwon, Hyun J., et al. *Sensing performance of protein C immunobiosensor for biological samples and sensor minimization* Comparative Biochemistry and Physiology Part A 132 (2002) 231-238.

Balcer, Heath I., et al. *Assay Procedure Optimization of a Rapid, Reusable Protein C Immunosensor for Physiological Samples* Annals of Biomedical Engineering. vol. 30, pp. 141-147, 2002.

Berlier, Judith E., et al. *Quantitative Comparison of Long-wavelength Alexa Fluor Dyes to Cy Dyes: Fluorescence of the Dyes and Their Bioconjugates* The Journal of Histochemistry & Cytochemistry vol. 51(12): 1699-1712, 2003.

Buschmann, Volker, et al. *Spectroscopic Study and Evaluation of Red-Absorbing Fluorescent Dyes* Bioconjugate Chem. 2003, 14, 195-204.

Lakowicz, Joseph R., et al. *Release of the self-quenching of fluorescence near silver metallic surfaces* Analytical Biochemistry 320 (2003) 13-20.

Du, Xinzhen, et al. *Comparitive study on fluorescence enhancement and quenching of europium and terbium chelate anions in cationic micelles* Spectrochimica Acta Part A 59 (2003) 271-277.

Krenn, Joachim R. *Nanoparticle waveguides: Watching energy transfer* Nature Publishing Group http://www.nature.com/nmat/journal/v2/n4/full/nmat865,html. Nature Mater., 2003, vol. 2, pp. 210-211.

Hong, Bin, and Kyung A. Kang, "Biocompatible, nanogold-particle fluorescence enhancer for fluorophore mediated, optical immunosensor," Biosensors and Bioelectronics (available online Jun. 2005). 2006, vol. 21, pp. 1333-1338.

Lakowicz et al., "Intrinsic Fluorescence from DNA can be enhanced by metallic particles", Biochemical and Biophysical Research Communications, 2001, vol. 286, pp. 875-879.

Spiker et al., "Preliminary study of real-time fiber optic based protein C biosensor", Biotechnology and Bioengineering, 1999, vol. 66, pp. 158-163.

Ulman, "Formation and structure of self-assembled monolayer", Chem. Rev., 1996, vol. 96, pp. 1533-1554.

Thomas, K. George and Kamat, Prashant V., Making Gold Nanoparticles Glow: Enhanced Emission from a Surface-Bound Fluoroprobe, J. Am. Chem. Soc. 2000, vol. 122, No. 11, pp. 2655-2656, 1999.

* cited by examiner

ENHANCEMENT OF SENSITIVITY OF FLUOROPHORE MEDIATED BIOSENSING AND BIOIMAGING

PRIORITY CLAIM

This is a divisional application of U.S. application Ser. No. 11/190,199, filed Jul. 26, 2005, which claims the benefit of U.S. Provisional Application Ser. No. 60/590,992, filed Jul. 26, 2004, under 35 U.S.C. §119.

FIELD OF THE INVENTION

A field of the invention is biosensing and bioimaging.

BACKGROUND OF THE INVENTION

Biomarkers used for disease diagnoses are usually present in bio-samples with a wide variety of other biomolecules, some of which are structurally homologous to the biomarkers themselves. In addition, the levels of the biomarkers in a sample are usually extremely low. Therefore, sensors to detect these biomolecules must be both very sensitive and specific.

Fluorophores have been valuable tools in biosensing/bioimaging for disease screening, diagnosis and monitoring. However, the low quantum yield (QY) of some of these fluorophores caused by non-radiative decay, especially by self-quenching, limits the effectiveness of these fluorophores in biosensing/bioimaging applications. Enhancement of the fluorescence can, therefore, improve the sensitivity of fluorophore-mediated biosensing and bioimaging.

SUMMARY OF THE INVENTION

Embodiments of the invention include a device and method for enhancing fluorescence emission in fluorophore-mediated biosensors. An exemplary method includes conducting a fluorophore-mediated sandwich immunoassay and exposing a flurophore-linked sandwich complex to an enhancing agent, such as a nanometal particle surrounded by a layer having a predetermined thickness (e.g., a self-assembled monolayer, surfactant or peptide), an organic, biocompatible solvent, or a combination of the nanometal particle with the self-assembled monolayer and the organic, biocompatible solvent. Another exemplary embodiment of the invention includes a biological sensor having enhanced fluorescence emission that includes an optical fiber having a fluorophore-mediated sandwich immunoassay disposed thereon, a chamber having at least one opening through which said fiber may extend, with an enhancing agent disposed in the chamber. The enhancing agent may be a nanometal particle a layer of predetermined thickness, an organic biocompatible solvent, or a combination the nanometal particle having the layer of predetermined thickness, and the organic, biocompatible solvent.

DETAILED DESCRIPTION OF THE PREFERRED EMBODIMENTS

Fluorescence of a fluorophore is normally limited by self-quenching of the free electrons in the fluorophore, thereby limiting the sensitivity of biosensors with which they are used. Embodiments of the invention reduce or eliminate this self-quenching, which enhances fluorescence emission of the fluorophore, thereby enhancing the ability to detect the presence of and quantify a target analyte. Fluorescence of some fluorophores and of fluorophore mediated biosensors is also enhanced significantly by biocompatible organic solvents. Devices and methods of the invention include exposing a fluorophore-mediated sandwich immunoassay to an enhancing agent, where the enhancing agent may be a nanometal particle having a layer of predetermined thickness, an organic, biocompatible solvent, or a combination of both a nanometal particle having a layer of predetermined thickness and an organic, biocompatible solvent.

Electrons of fluorophores that are normally involved in self-quenching upon photoexcitation may be coupled to strong surface plasmon polaritron fields of metallic nanoparticles, e.g., gold, silver, platinum and copper nanoparticles. Fluorescence can be maximized when a fluorophore is placed at a particular distance from the nanoparticle, wherein the particular distance may be empirically determined.

Embodiments of the invention exploit the surface plasmon polaritron fields of metallic nanoparticles, such as nanogold particles, nanosilver particles, nanoplatinum particles and nanocopper particles, for example, to enhance fluorescence. When plasmon rich, sharp metal tips or nanometal particles are placed at a particular distance from a fluorophore in accordance with the invention, they enhance the fluorescence by several fold, possibly by removing the cause of static or Foester quenching. This fluorescence enhancing effect can be artificially induced when a fluorophore is placed next to a metal particle treated with, for example, a self-assembled monolayer at a particular thickness. It is anticipated that the metal nanoparticle may be treated with a number of substances to obtain a layer having a predetermined thickness, such as a self-assembled monolayer, a surfactant, or a peptide, to name a few. The self-assembled monolayer will be discussed herein for purposes of illustration.

When placed at an appropriate, predetermined distance from a fluorophore, the metallic nanoparticles can effectively enhance fluorescence by transferring the free electrons of the fluorophore, electrons normally used for self-quenching, to the strong surface plasmon polaritron fields. If the metallic nanoparticle is placed too close to the fluorophore, the metallic nanoparticle extracts all electrons in the excited state from the fluorophore, including the ones for radiative emission. Alternatively, when the metallic nanoparticle is placed too far from the fluorophore, the surface plasmon polaritron fields may not reach the fluorophore, and there will be no effect on the resulting fluorescence intensity. However, when the appropriate predetermined distance is maintained between the metallic nanoparticle and the fluorophore via a predetermined mechanism, the fluorescence may be enhanced as the electrons normally used for self-quenching are transferred.

With application of embodiments of the invention, the sensitivity of the fluorophore mediated biosensor increases by several folds, which enables sensors with much higher sensitivity; increased accuracy diagnoses—fewer false positives or negatives; and minimization of the sensor size and assay time. Embodiments of the invention provide—either fluorescence-enhacing nanometal particles, organic, biocompatible solvents, or a combination of both.

In embodiments using nanometal particles only, the invention contemplates using a variety of metallic nanoparticles, such as nanogold particles and nanosilver particles, nanoplatinum particles and nanocopper particles. However, for exemplary purposes, nanogold particles and nanosilver particles will be discussed herein for purposes of illustration. In a first preferred embodiment, a self-assembled monolayer of a predetermined thickness on the nanogold surface ("nanogold particle-self-assembled monolayer") or nanosilver particle surface ("nanosilver particle-self-assembled monolayer") is used to maintain the appropriate predetermined distance between the nanogold particle or nanosilver particle and the fluorophore. The self-assembled monolayer may include one of a plurality of molecules, preferably those water soluble, organic molecules with a thiol or amine terminal group in their structures, that may self-assemble onto the nanoparticles. For example, two such molecules are L-Glutathione and 16 mercaptohexadecanoic acid.

Other embodiments of the invention utilize one or more organic solvents to affect the fluorescence intensity in biosensing applications, even without exposure to nanometal particles having self-assembled monolayers. To maximize the fluorescence, embodiments of the invention include biocompatible organic solvents combined with metallic nanoparticles, such as nanogold particle reagents (NGPRs). Experiments have shown that organic solvents enhance fluorescence intensity. Without limiting the invention in any way, and only as a potential explanation of the mechanism for the enhancement, it is believed that organic solvents, such as ethanol, affect fluorescence intensity by 1) shifting the excitation/emission spectra of the fluorophore, 2) by the isomerization of the fluorophore, 3) by shrinking the fluorophore tagged proteins, or 4) by a combination of the three mechanisms. Preferred solvents include a solution that includes nanometal particles of less than 100 nm having self-assembled monolayers assembled thereon.

Still other embodiments include the use of one or more organic solvents in addition to maintaining a predetermined distance between the nanometal particle and the fluorophore using a self-assembled monolayer, where the effect of solvent on the level of fluorescence enhancement is additive. In one embodiment, use of the combination of nanogold particles having a self-assembled monolayer and a biocompatible solvent increase the signal of a fiber-optic biosensor as much as ten times, and can accurately quantify various cardiac markers at a tens of picomolar level.

Yet another preferred embodiment includes one or more organic solvents in combination with a SAM of a predetermined thickness to enhance fluorescence.

Embodiments of the invention are contemplated for sensing applications involving a virtually unlimited number of target analyte, especially proteins such as cardiac markers. For example, Cardiac Troponin I (cTnI) and Human B-type natriuretic peptide (BNP) are two cardiac markers that are very important for rapid and accurate heart attack diagnoses and prognosis. Protein C is a plasma anticoagulant and the accurate quantification can diagnose the genetic disorder, Protein C deficiency. The same principals may be used to diagnose various cancers.

Figure 1A:
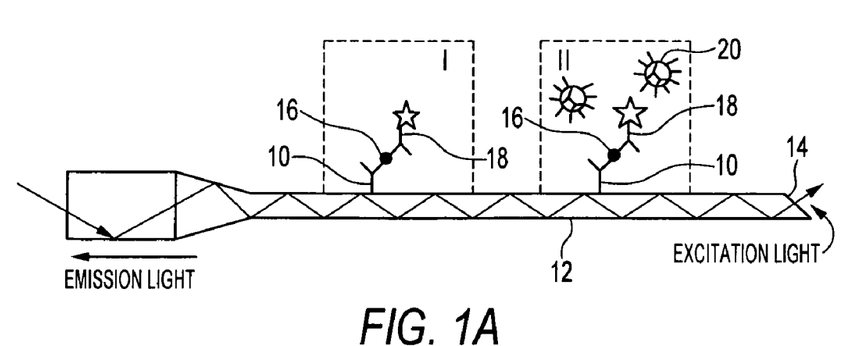
FIG. 1A is a schematic diagram comparing fluorescence emission between (I) conventional fiber optic immuno-sensing and (II) immuno-sensing using nanometal particles linked with self assembled monolayers according to an embodiment of the invention.

Turning to FIG. 1A, for example, a first embodiment of the invention contemplates the use of nanogold particles of a particular size placed at a predetermined distance from a fluorophore in flurophore-mediated biosensing (immuno-optical protein C biosensor, for example) and bioimaging applications. While the size of the nanogold particles may vary to suit individual applications and are contemplated to include sizes ranging from 1 nm to 100 nm, nanogold particles ranging from 2 nm to 10 nm are optimal, preferably approximately 5 nm. A fluorophore-mediated immunoassay is conducted, with a 10 monoclonal antibody (1° Mab) 10 is immobilized on an optical fiber 12, such as a quartz fiber. The fiber may optionally include a beveled tip 14, polished to a predetermined angle, such as 45°. After exposure to a sample believed to include a target analyte 16 (e.g., protein C), a fluorophore-conjugated 2° monoclonal antibody (2° Mab) 18, such as Cyanine 5 (CY5®)-2° Mab, for example, binds the target analyte 16. As illustrated in box I, a fluorophore 19, which is represented during emission by a star-shape, emits fluorescence upon the exposure to excitation light at a certain quantum yield. As illustrated in box II, when the fluorophore-mediated sandwich complex is applied with nanogold particles-self-assembled monolayers 20, the fluorescence is enhanced upon exposure to excitation light. The thickness of the self-assembled monolayers is an optimal thickness to maximize the enhancement and in the instant embodiment, and is contemplated to be between 1 nm and 10 nm, preferably between 1 nm and 3 nm, with approximately 2 nm providing maximum enhancement.

Figure 1B:
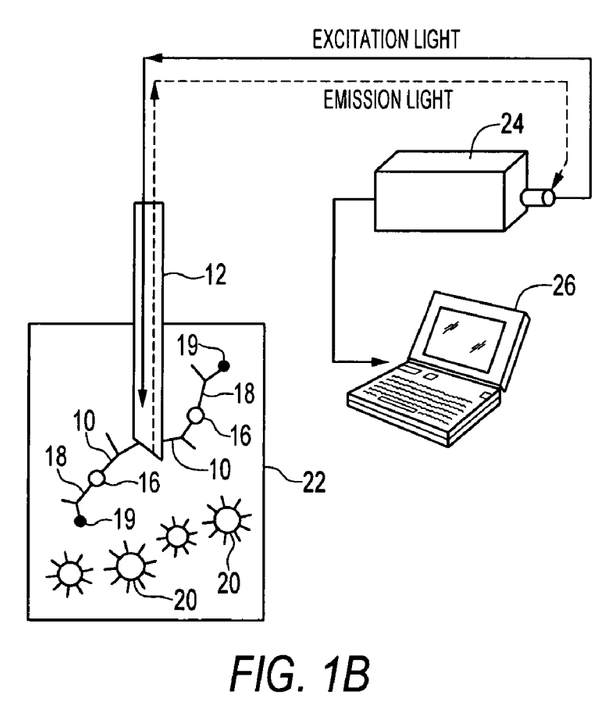
FIG. 1B is a schematic diagram illustrating the fluorescence measurement for free fluorophores in solution.

FIG. 1B illustrates an exemplary system in which a sensor may be used. The tip 14 of the fiber 12 is immersed in a buffer containing nanogold particles-self-assembled monolayer. At an end of the fiber 12 opposite the tip 14, the fiber is operably coupled to a fluorometer 24 that emits excitation light of a predetermined wavelength, and receives emission light from the fiber. The fluorometer 24 is preferably operably coupled to a computer 26 or other data acquisition device. Fluorescence emissions can accordingly be measured and the presence, absence and quantification of even small amounts of a target analyte may be ascertained.

Figure 2:
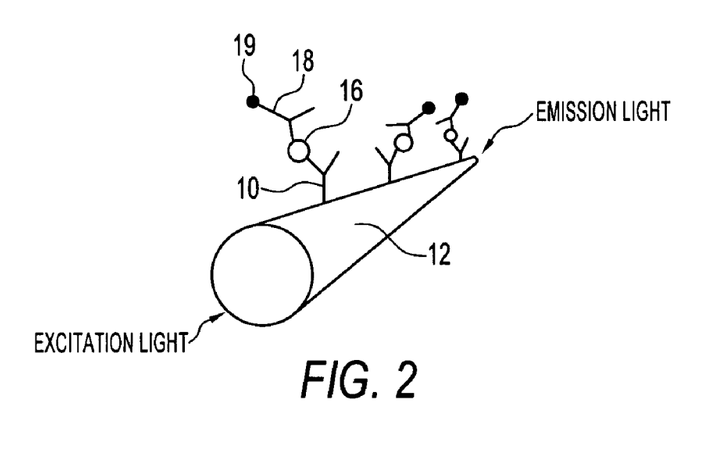
FIG. 2 is a schematic diagram illustrating an exemplary biosensor, Protein C Sensor, according to one embodiment of the invention.

By way of example only, a Protein C (PC) immuno-biosensor 28 for diagnosing a disease, PC deficiency, will be particularly described using FIG. 2 to illustrate. A distal end 30 of the quartz fiber 12 is tapered to increase evanescent signal retention and this portion of the fiber is encased in the chamber 22, which is a capillary sensor chamber. A surface of the fiber 12 is immobilized with 1° Mab 10 against PC. When a sample is injected into the chamber 22, the PC 30 binds specifically to 1° Mab 10 on the fiber surface with a high affinity. Then, the fiber 12 is preferably washed to remove unbound molecules. Next, the system is probed with another type of PC monoclonal antibodies that are tagged with a fluorophore 34, CY5®-2° Mab 36. After the reaction, excitation light, preferably of a wavelength of approximately 635 nm, is applied to the fiber 12. The CY5®-2° Mab 36 bound to PC 30 generate an emission signal of approximately 667 nm that is preferably interrogated by a long pass filter 38 placed before a silicon detector (not shown). Then, the fluorescence intensity is correlated with the PC concentration. Since the 1° Mab 10 is covalently bound to the fiber 12, the fiber can be reused after adsorbed PC are eluted from the system using appropriate elution and regeneration buffers. The sample chamber 22 is very small (50-200 μl), requiring only a small sample volume per assay. The fluorescence generated from the immuno-optical biosensor is measured by the fluorometer 24.

Figure 3:
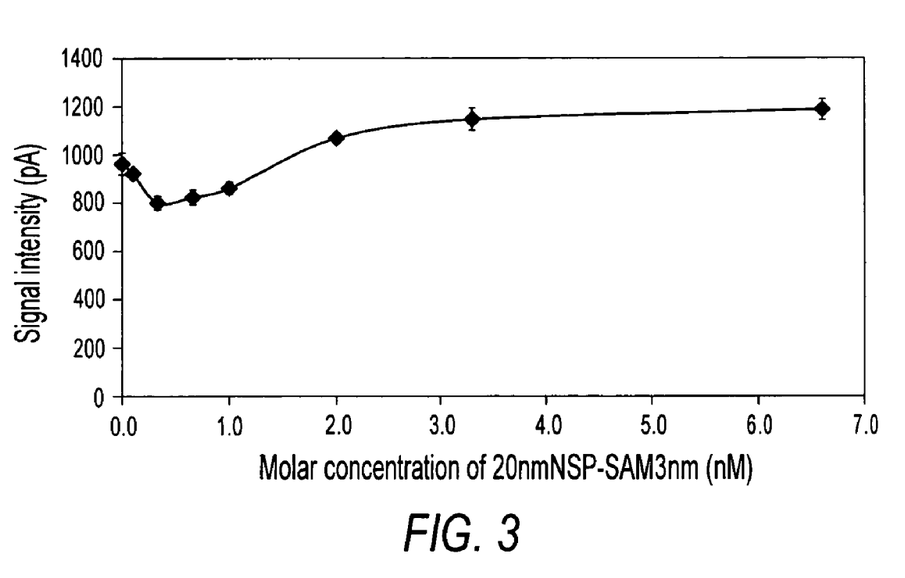
FIG. 3 is a graph illustrating free fluorophore enhancement by 20 nm nanosilver particle-self-assembled monolayer 3 nm using fiber tip systems, where CY5® fluorophore concentration is fixed as 66 nM.

A preferred embodiment uses nanosilver particles as an enhancer. While different sized nanosilver particles may be used, an approximately 20 nm sized nanosilver particles is illustrated, since it is the smallest commercially available nanosilver particle, though alternatively sized nanosilver particles are contemplated to suit individual applications and as smaller particles become commercially available. FIG. 3 illustrates the enhancement of free fluorophore by nanosilver particles, and the mixture of the CY5® and 20 nm nanosilver particles with the CY5®/nanosilver particles ratio of 10/1 provided the highest enhancement of 23.3% compared to the pure CY5® solution.

Figure 4:
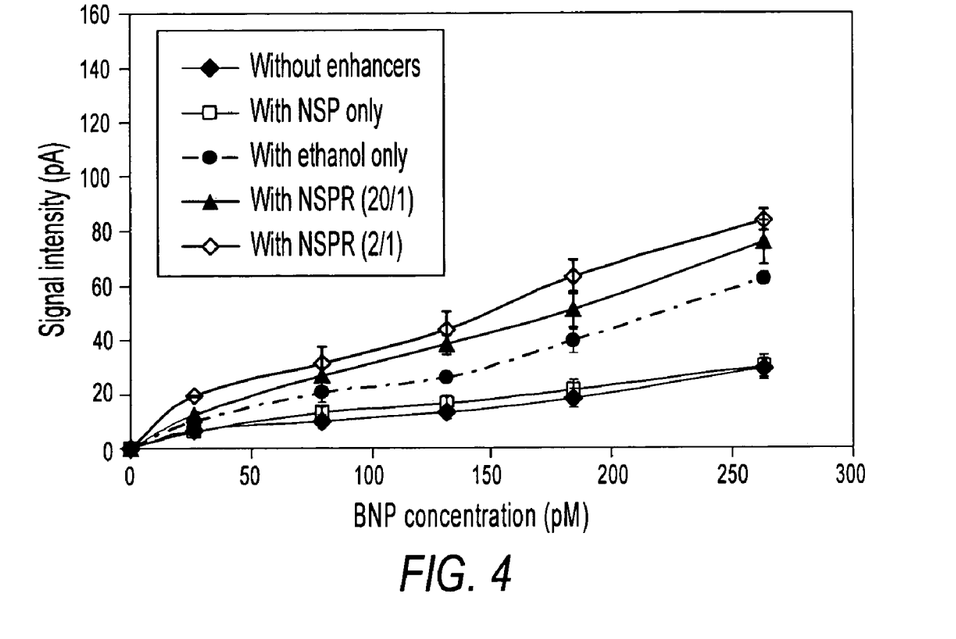
FIG. 4 is a graph illustrating BNP (a cardiac biomarker) sensing performance.

Twenty nm nanosilver particles and the nanosilver particle reagent (NSPR) are also contemplated for use with the fluorophore-mediated BNP biosensor, as illustrated in FIG. 4. A 1.5 cm sensor was selected at 3 and 4 min incubation times for sample and 2° Mab, 1.2 cm/sec flow velocity, and a dye/nanosilver particles ratio of 20/1 and 2/1. The bottom line represents the sensing results without any enhancers. Compared to this control, 4%~35% enhancements were observed by 20 nm nanosilver particles only, 100%~14% enhancement by ethanol, the solvent only. The NSPR with fluorophore/nanosilver particle ratio of 20/1 provided 85%~190% enhancement, while ratio of 2/1 provided the highest enhancement 185%~245%. Therefore, these results confirm that the nanosilver particles and NSPR can also provide the fluorescence enhancements for free flourophore or fluorophore mediated biosensing.

Figure 5:
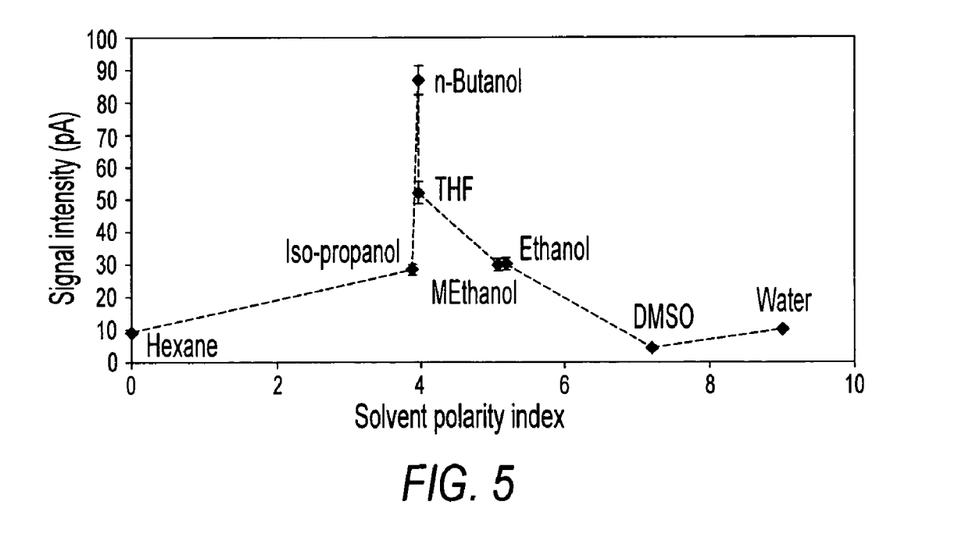
FIG. 5 is a graph illustrating the effect of the solvents with various polarity on fluorescence enhancement of biosensing.

Other embodiments of the instant invention include biocompatible solvents that enhance the fluorescence signal. Numerous solvents are anticipated, preferably those solvents that are biosensor compatible (i.e., not affecting the antibody affinity) and which do not prevent reusability of the fiber. While numerous organic solvents are contemplated for use with the invention, one preferred solvent is ethanol. FIG. 5 is a graph providing a comparison in fluorescence enhancement for several different solvents, including hexane, iso-propanol, n-butanol, THF, methanol, ethanol, DMSO and water. A 1.5 cm BNP sensor was used, with 1.2 cm/sec velocity, 3 and 4 min incubation times, 0.5 ng/ml BNP in plasma.

Figure 6:
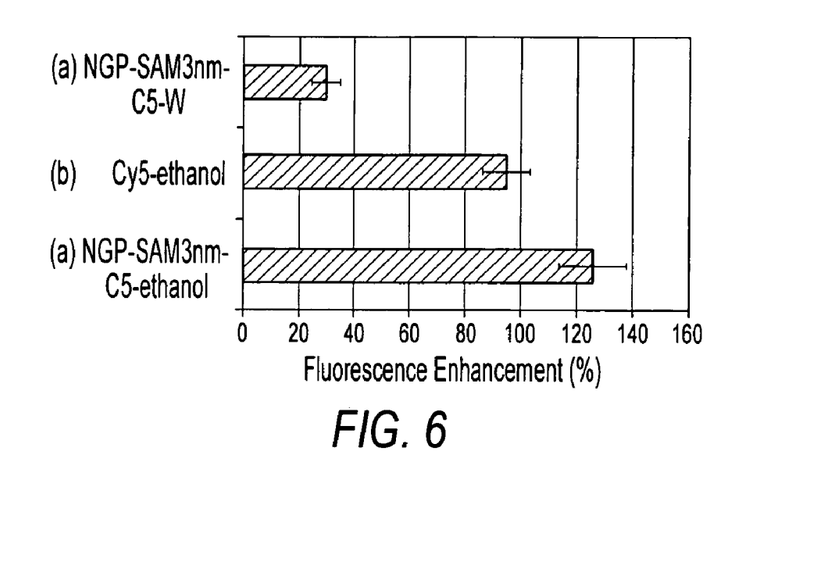
FIG. 6 is graph illustrating the effect of nanogold particle-self-assembled monolayer, ethanol, or nanogold particle-self assembled monolayer-ethanol combination on fluorescence enhancement.

One particularly advantageous solvent is ethanol, which will be discussed for exemplary purposes. FIG. 6 illustrates the fluorescence enhancement when the fluorophore CY5® is mixed with (a) nanogold particle-self-assembled monolayer only; (b) ethanol only; and (c) nanogold particle-self-assembled monolayer and ethanol together. Experimental conditions included CY5® concentration of 0.066 μM, and a CY5®/nanogold particle ratio of 20/1. As can be seen in the figure, the enhancement by ethanol is even higher than that by nanogold particle-self-assembled monolayer and when nanogold particle-self-assembled monolayer and ethanol are combined together the degree of the enhancement seems to be additive.

To illustrate with a specific example, the Protein C (PC) sensing system, a fluorophore such as either CY5® or ALEXA FLUOR® 647 (AF647) is conjugated with 2° Mab. The invention should not be construed as being limited to the fluorophores CY5® and AF647, as additional fluorophores are also contemplated for use with the invention. For example, ATTO 647, BODIPY® 650/665 and DY-636 are additional potential fluorophores that may be used with the invention, to name a few. CY5® and AF647 were selected because they have very similar maximum excitation wavelengths (647 and 650 nm, respectively), but the quantum yield for AF647 is approximately twice of that for CY5®. Therefore, the enhanced signal intensity for AF647 by nanogold particle-self-assembled monolayers is expected to be lower than that for CY5®.

Figure 7:
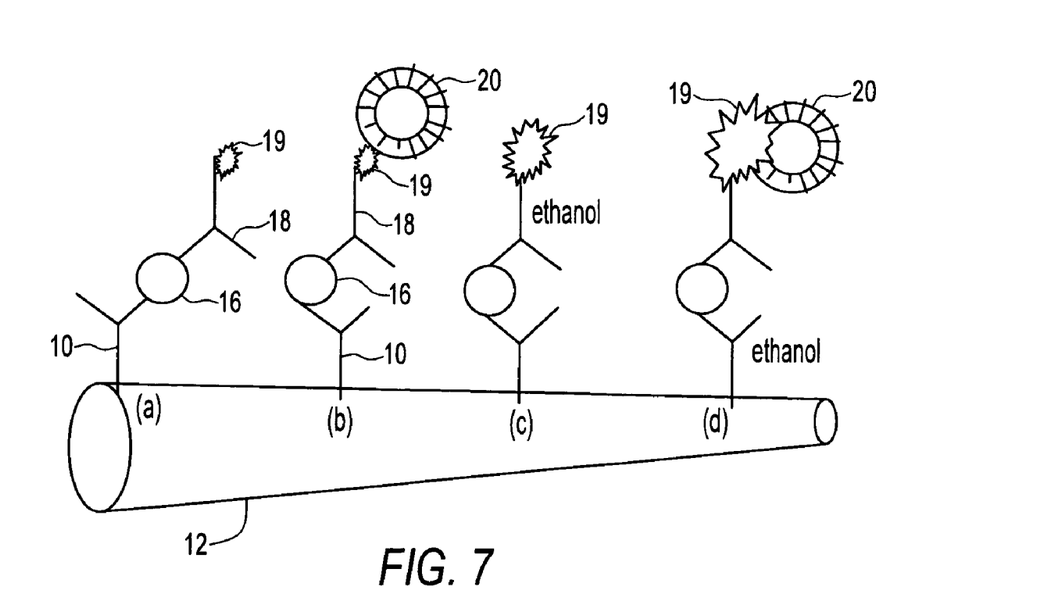
FIG. 7 is a schematic diagram of the test for fluorescence enhancement in fiber optic immuno-biosensing: (a) the usual PC immuno sensing; (b) sensing with nanogold particle-self-assembled monolayer only; (c) sensing with ethanol only; and (d) sensing with both nanogold particle-self-assembled monolayer and ethanol.
Figure 8:
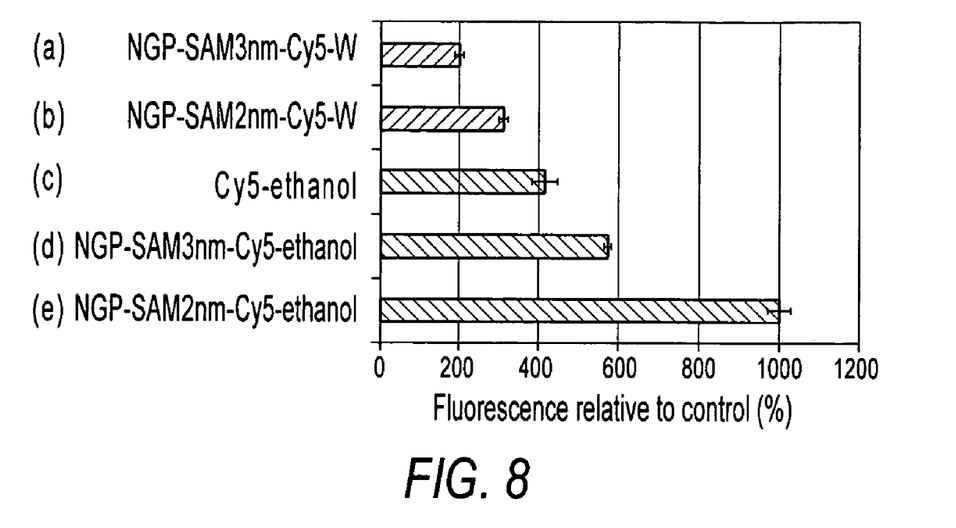
FIG. 8 is a graph illustrating fluorescence enhancement using only a self assembled monolayer (a) and (b), and fluorescence enhancement using a nanogold particle-self-assembled monolayer-ethanol (d) and (e).

The intensity of the emission light generated from fluorophore-2° Mab quantifies the amount of PC in the sample. If the emission intensity by fluorophore-2° Mab is enhanced by even a few folds, then the sensor can become much more sensitive by increasing the signal to noise ratio (S/N ratio). Four different test cases are as shown in FIG. 7: (a) the control—a conventional PC sensing protocol; (b) applying only the nanogold particle-self-assembled monolayer after the completion of the CY5®-2° Mab reaction; (c) applying only ethanol; and (d) applying the mixture of the nanogold particle-self-assembled monolayer and ethanol. FIG. 8 illustrates the results of these cases of biosensing. In all cases, the enhancement in biosensing is several folds more than that with the free form of fluorophores. Also, the self-assembled monolayer thickness affects the degree of enhancement for both cases with only nanogold particle-self-assembled monolayer (in FIG. 8, (a) and (b)), and nanogold particle-self-assembled monolayer-ethanol (in FIG. 8, (d) and (e)), as in the free form. Again, the enhancement by nanogold particle-self-assembled monolayer and ethanol together shows the additive effect, e.g., as high as ten times of enhancement.

According to one embodiment of the invention, 5 nm sized nanogold particles are used. Nanogold particles are linked (treated) with two different lengths, 2 or 3 nm, of a self-assembled monolayer (SAM) and mixed with fluorophores, CY5® or AF647. Again, these two fluorophores were selected because they have very similar maximum excitation wavelengths.

Figure 9:
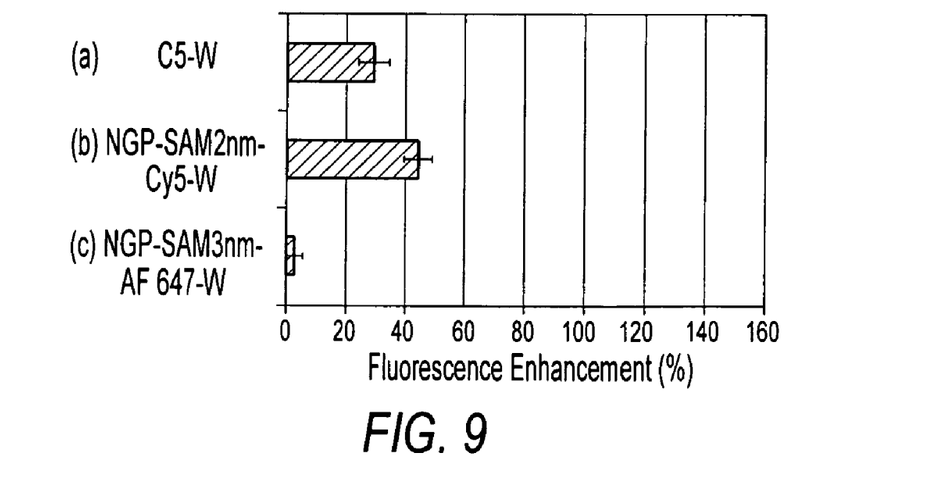
FIG. 9 is a graph illustrating fluorescence enhancement of (a) CY5®-W; (b) nanogold particle-self-assembled monolayer-2 nm-CY5®-Water; and (c) nanogold particle-self-assembled monolayer-3 nm-AF647-W.

The fluorescence from the mixture of fluorophore and nanogold particle-self-assembled monolayer was first measured using the tip of an optical fiber, as shown in FIG. 1B, and compared with that without nanogold particle-self-assembled monolayer. The fluorophore concentration in the buffer solution was 0.066 μM and the molar concentration ratio of nanogold particle-self-assembled monolayer to the fluorophores was 1:20. The ratio between the fluorophore and the gold particles affects the degree of enhancement and this ratio provides a clear enhancement. FIG. 9 summarizes the results of the level of the fluorescence enhancement when (a) CY5® is mixed with the NGPs linked with 3 nm SAM (SAM3 nm) in a water base buffer (W); (b) CY5® with the NGPs linked with 2 nm SAM (SAM2 nm) in the buffer; and AF647 is mixed with the NGPs linked with 3 nm SAM in the buffer. Two types of SAMs at thickness of 2 (MW=288) and 3 (MW=1701) nm, had been used. They are 16-Mercaptohexadecanoic acid and Tannic acid. The control is the fluorescence intensity from each dye molecules at the same concentration, without nanogold particle-self-assembled monolayers. From this figure, it is shown that the SAM thickness affects the level of the enhancement (2 nm enhances better). The tests also reveal possible enhancement by the fluorophore with a lower quantum yield (CY5®) is more than that of the fluorophore with higher one (AF647).

EXPERIMENTS AND RESULTS

Materials and Methods

Nanogold Particles-Self-Assembled Monolayer and NGPR Preparation

Nanogold colloids, which are nanogold particles (2, 5 and 10 nm) coated with tannic acid (surfactant, approximately 3 nm) were obtained. The thickness of a surfactant layer or self-assembled monolayer was theoretically estimated. L-Glutathione (approximately 1 nm) and 16 mercaptohexadecanoic acid (approximately 2 nm) used as self-assembled monolayers. The self-assembled monolayer of L-glutathione or 16 mercaptohexadecanoic acid was linked on the surface of the nanogold particles by dissolving these molecules in distilled water or dimethyl sulfoxide; transferring them to the nanogold collois; heating the mixture up to 70° C.; stirring them for 5 h; and purifying the products to eliminate the unreacted self-assembled monolayer molecules and replaced surfactant molecules. The NGPRs were produced by mixing the nanogold particles-self-assembled monolayers and the solvent to be tested.

Biosensor Preparation

Fluorophores, FLUOROLINK™ Cyanine 5 (CY5®) and ALEXA FLUOR® 647 (AF647), were obtained. The CY5® or AF647 solution was prepared by dissolving the solid fluorophores in distilled water. A fluorometer with a long pass 670 nm filter inside and quartz fibers were used for sensors. Protein C and anti-PC monoclonal antibodies were obtained. Human B-type natriuretic peptide (BNP) and anti-BNP monoclonal antibodies were obtained. Cardiac Troponin I (cTnI) and anti-cTnI monoclonal antibodies were obtained. The PC sensor, PC samples, and fluorophore conjugated second antibody (fluorophore-2' Mab) were prepared.

Assay Protocol

The fluorescence of the free fluorophore in the phosphate buffer solution (PBS; control) or in the mixtures with nanogold particles-self-assembled monolayers or NGPRs was measured using a quartz fiber whose tip was polished at 45°. The fluorescence enhancement was also investigated with a fiber-optic PC sensor, which was developed for PC deficiency diagnosis. The sensor performs a fluorophore-mediated sandwich immunoassay on the sensor surface, and the fluorescence intensity is correlated with the PC concentration in blood plasma. Conventional assay protocol was used as a control: (1) sample injection and convective incubation, 0.5 min; (2) sensor washing and baseline measurement, 1 min.; (3) fluorophore-2° Mab injection and convective incubation, 2 min. (4) sensor washing and fluorescence measurement, 1 min.; (5) sensor regeneration, 1 min, and then the sensor is ready for the next assay. The signal used for the analyte quantification is the fluorescence measured in the step (4) subtracted by the baseline signal measured in the step (2).

For testing nanogold particles-self-assembled monolayers, solvents, or NGPRs, the protocol was modified to (1') nanogold particles-self-assembled monolayers, solvents or NGPRs injection and baseline measurement, 0.5 min; (2') sensor washing 0.5 min; (3') sample injection and convective incubation, 0.5 min; (4') sensor washing, 0.5 min; (5') fluorophore-2° Mab injection and convective incubation, 2 min; (6') sensor washing, 0.5 min., (7') nanogold particles-self-assembled monolayers, solvents or NGPRs injection and fluorescence measurement, 0.5 min., (8') sensor washing and regeneration, 1.5 min. The fluorescence used for PC quantification is the value measured in the step (7') subtracted by that measured in the step (1').

Results and Discussion

Effects of the distance between a fluorophore and an NGP, and the NGP size on the fluorescence enhancement were studied. Since the concentration of the fluorophore and the NGP in a sample may also determine the distance, their concentrations were first adjusted to place them close enough to interact but not too crowded for quenching. The concentration ranges of the fluorophore and the nanogold particles used for this study were $10^{-8}$ to $10^{-7}$ and $10^{-10}$ to $10^{-7}$M, respectively. The fluorescence enhancement is defined as the increase in fluorescence by the enhancer divided by the fluorescence intensity without the enhancer.

The Effect of the Distance Between an NGP and a Fluorophore

Figure 10A:
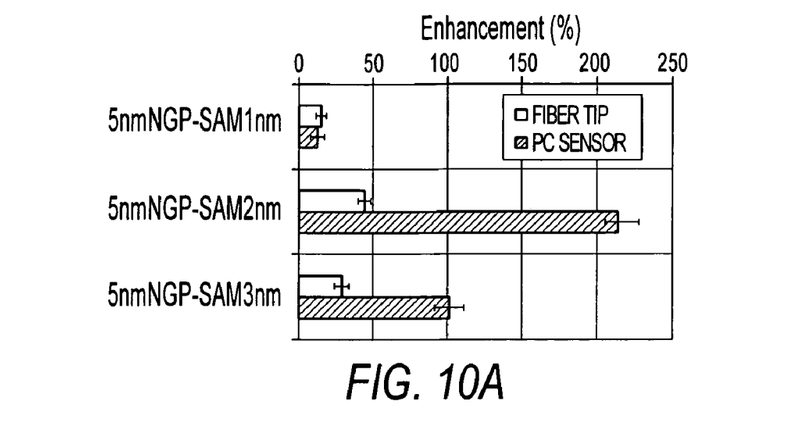
FIG. 10A is a graph illustrating the effect of self-assembled monolayer thickness on fluorescence enhancement for the free CY5® and the CY5® mediated PC sensing.
Figure 10B:
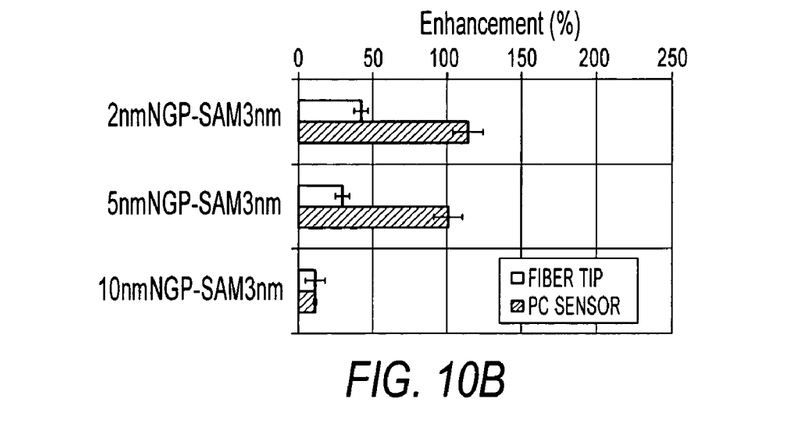
FIG. 10B is a graph illustrating the effect of nanogold particle size on the fluorescence enhancement for the free CY5® and the CY5® mediated PC sensing.
Figure 10C:
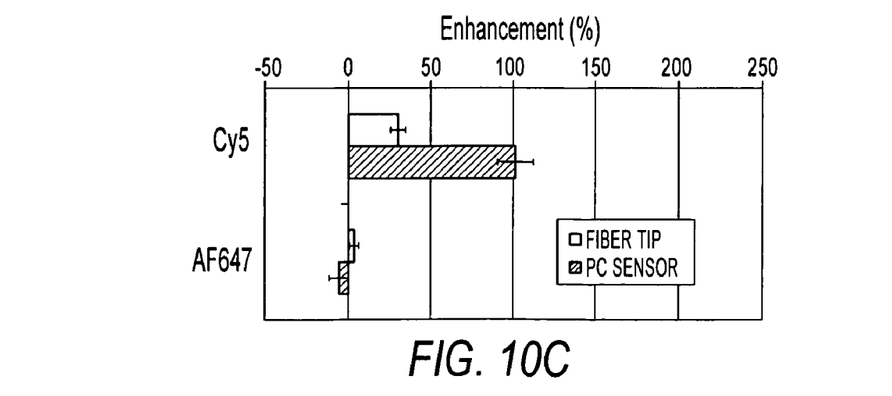
FIG. 10C is a graph illustrating the effect of nanogold particle size on the fluorescence enhancement for the free CY5® and the CY5® mediated PC sensing.

Turning to FIGS. 10A-10C, in this study, the distance between a fluorophore and a nanogold particle was adjusted by the thickness of a self-assembled monlayer immobilized on the NGP surface. For this test, the nanogold particles size was kept constant at 5 nm. The thicknesses of the self-assembled monolayers tested were 1, 2 or 3 nm (L-glutathione, 16-mercaptohexadecanoic acid, and tannic acid, respectively). The nanogold particle-self-assembled monolayer was then applied to the free CY5® or the CY5® mediated PC biosensor and the fluorescence was measured (FIG. 10A). The ranges of the enhancement were 15~44% for the free CY5® and 12~215% for the PC sensing. The PC sensing results showed a trend qualitatively similar to those of the free fluorophore, but with several fold higher enhancements. For both cases, the self-assembled monolayer thickness of 2 nm provided the highest enhancement (44±4 and 25±8%, respectively). Although there were enhancements, 1 nm may have been too close to prevent reduction in radiative emission, and 3 nm may have been too far to transfer the electrons for effective enhancement.

The Effect of the Nanogold Particle Size

The effect of the nanogold particle size (2, 5 or 10 nm) was investigated at a constant SAM thickness of 3 nm (FIG. 10B). The enhancement for the free CY5® by 2, 5 and 10 nm nanogold particles were 42±5, 30±5, and 11±7%, respectively, showing a reduced enhancement as the nanogold particle size increased, possibly due to the differences in the surface plasmon polaritron field intensity for the nanogold particles of different size. For the PC biosensing, the enhancements were 115±10, 102±10, and 12±1%, respectively, showing a similar trend but much higher enhancements than those of the free fluorophore, as in the previous case. The higher enhancement in biosensing may be because free fluorophores suspended in solution interact with the nanogold particles in a three-dimensional space, not necessarily staying at the proximity of the fiber tip, while biosensing provides the sensor-surface-bound fluorophores for the nanogold particles to react.

Among the nanogold particle-self-assembled monolayers test (nanogold particle size of 2, 5 and 10 nm and self-assembled monolayer thickness of 1, 2 and 3 nm), 5 nm nanogold particles linked with 2 nm self-assembled monolayers (5 nmNGP-SAM 2 nm) were found to be the best enhancer.

The Effect of the Quantum Yield of a Fluorophore

Because it has been theorized that the fluorescence enhancement by nanogold particles is by retrieving the fluorescence that is normally self-quenched, it was expected that the amount of the enhanced fluorescence would depend upon the quantum yield (QY) of a fluorophore. To verity the theory, two fluorophores with the similar excitation/emission wavelengths, but with different QYs, were tested. CY5® (excitation/emission wavelengths: 649/670 nm) used in previous studies has a QY of 0.28. AF647 has excitation and emission wavelengths (649/666 nm) very similar to those of CY5®'s, but has a QY of two times greater than that of CY5® The fluorescence enhancement of free AF647 by 5 nm nanogold particle-self-assembled monolayer 3 nm were studied and the results were compared with those of CY5®'s. Free AF647 exhibited a significantly less enhancement (3±3%) than that of free CY5® (30±5%). Also, in the AF647 mediated biosensing, as expected, there was very little enhancement. These results confirmed the hypothesis that the level of fluorescence enhancement by nanogold particles-self-assembled monolayers depends on the QY of the fluorophore.

The Solvent Effect

Various physical/chemical properties of organic solvents, such as viscosity, polarity, etc., may also affect the fluorescence. Three solvents which were considered to be not too harsh to biomolecules were ethanol, methanol and THF. These solvents were tested. When free CY5® was dissolved in ethanol, 92±4% enhancement was obtained, while signal reduction was exhibited in methanol and THF. This may be caused by the different solvent polarity and the behavior of hydrogen-bonds. However, 318±19, 166±21, and 434±32% of enhancements were achieved in PC sensing by ethanol, methanol and THF, respectively, implying the presence of other enhancing mechanisms for immobilized, protein-linked fluorophores. Although THF showed the highest enhancement in PC sensing, it affected the biosensor reusability (reduced from 7 to 4 times), possibly by permanently denaturing of 1° Mab molecules on the sensor surface. Ethanol appeared to be a desired enhancer because it did not affect the reusability. n-Butanol was found to be an even better enhancer. It also worked very well with AF647 both in the free form (90±4% enhancement) and the PC sensing (>100%), while the fluorescence of this fluorophore was not enhanced by nanogold particles-self-assembled monolayers (FIG. 10C). This indicates that the enhancement mechanism of solvents is different from that of the nanogold particles-self-assembled monolayers.

The Enhancement by NGPR

Figure 11A:
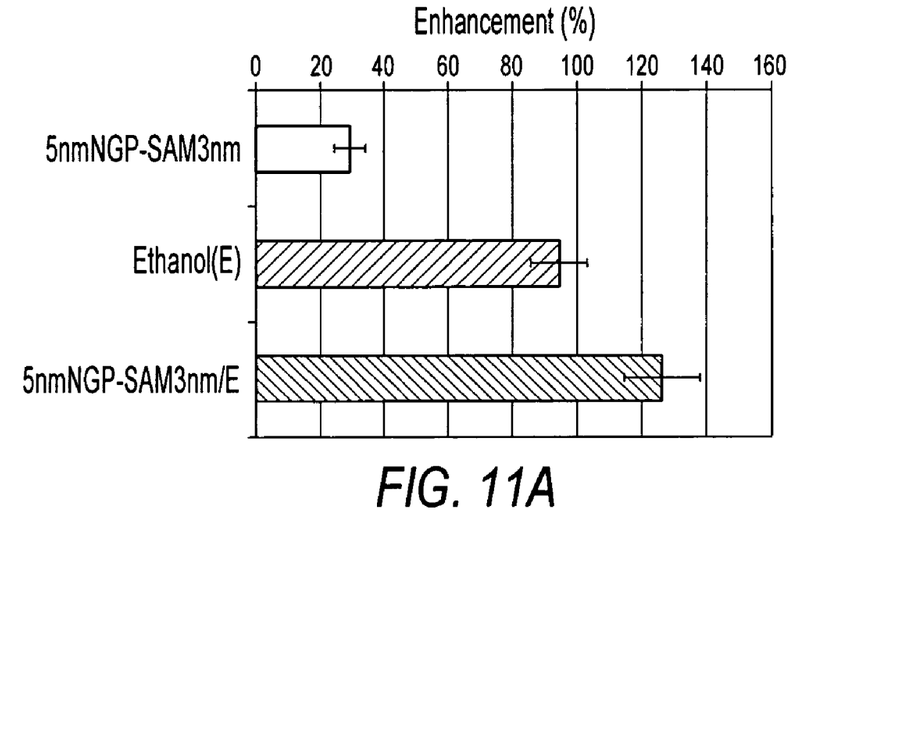
FIG. 11A is a graph illustrating the effect of nanogold particle-self-assembled monolayer, ethanol and NGPR on fluorescence enhancement of free CY5®.
Figure 11B:
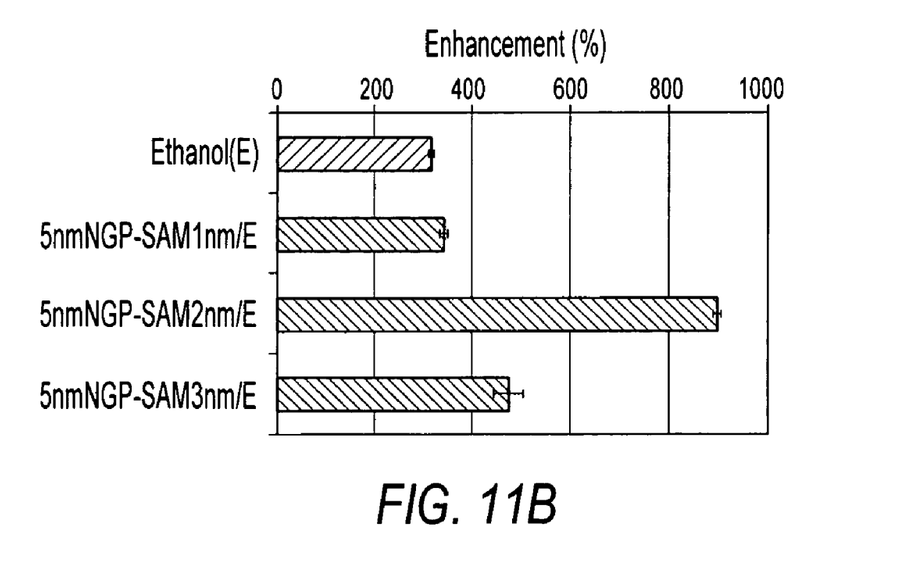
FIG. 11B is a graph illustrating the effect of ethanol and NGPRs with different self-assembled monolayers on fluorescence enhancement in PC sensing.

To maximize the enhancment effect, the two enhancers, the nanogold particles-self-assembled monolayers and the solvent, were mixed (NGPRs) and tested for their enhancement capacity. For 5 nm nanogold particles-self-assembled monolayers 3 nm mixed with ethanol, a 126±12% enhancement was demonstrated for freeS CY5®, which appeared to be additively contributed from the enhancement by 5 nm nanogold particles-self-assembled monolayer 3 nm (30±5%) and by ethanol (94±9%) (FIG. 11A). Measurements were also performed for PC sensing with 5 nm nanogold particle of various self-assembled monolayer thickness, for both free fluorophores and PC sensing the trend of the enhancement by these NGPRs was consistent by nanogold particles-self-assembled monolayers without ethanol (FIG. 10A). Quantitatively, the enhancement level for PC sensing with NGPRs was, again, several fold greater. For 5 nm nanogold particles-self-assembled monolayers 3 nm in ethanol, as an example, a 475±10% of enhancement was obtained, which was the combined effect by 5 nm nanogold particles-self-assembled monolayers 3 nm (102±10%) (FIG. 10A) and that by ethanol (318±31%). Ethanol is known to tightly fold proteins. Since the sensing principle of the immuno-biosensing is based on the retrieval of the fluorescent signals within the evanescent field, it was speculated that the ethanol may shrink the sandwich complex. As a result, fluorophore tagged 2° Mab may get closer to the sensor surface and the sensor retrieves more fluorescence per bound target biomarker. The protein structure change by ethanol is also known to be reversible and the application of ethanol, in fact, had no effect on the reusability of the PC sensor. PC sensing with 5 nm nanogold particles-self-assembled monolayers 2 nm in ethanol demonstrated the highest fluorescence enhancement, showing signal ten times stronger (898±28% enhancement) than that without any enhancers.

The Cardiac Marker Biosensing with NGPR

Figure 12A:
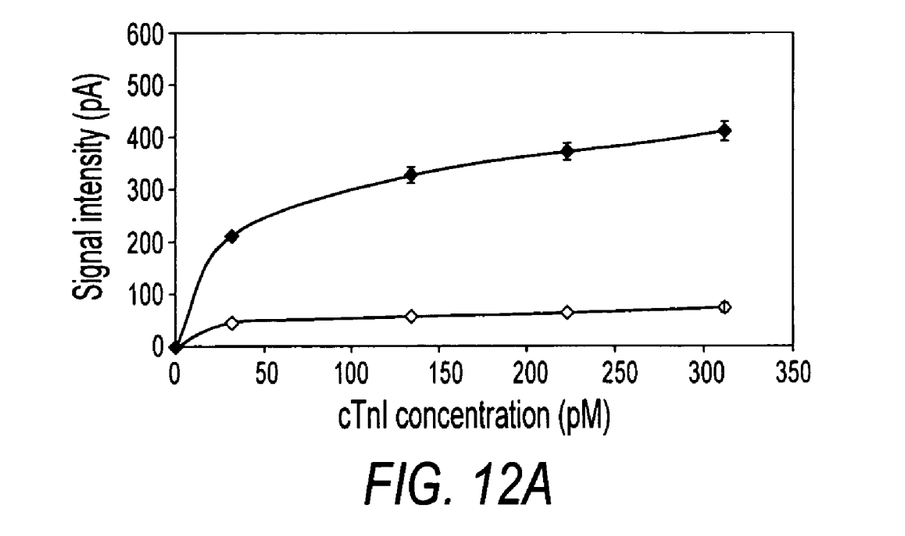
FIG. 12A is a graph illustrating the effect of NGPR on cardiac biomarker (cTnI) sensing.
Figure 12B:
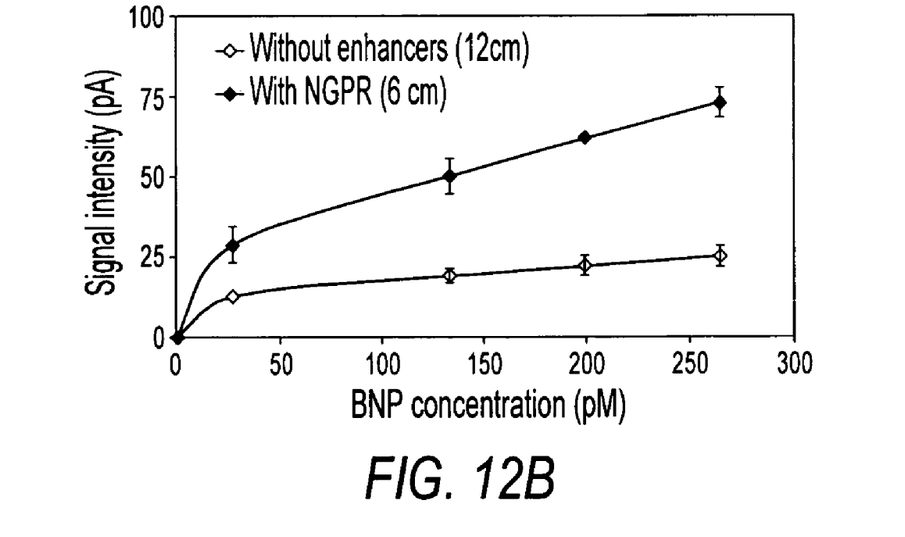
FIG. 12B is a graph illustrating the effect of NGPR on cardiac biomarker (BNP) sensing.

Fiber-optic biosensors are currently being developed to quantify cTnI and BNP in plasma, in their clinically significant ranges (31-310 and 26-260 pM), respectively. Because of their low target concentrations, without enhancers, the sensing performances of these two sensors were studied with 12 cm sensors and 10 min/10 min incubations. These markers were also measured with an NGPR (5 nm nanogold particles-self-assembled monolayers 2 nm in ethanol) by a 6 cm sensor with 5 min/S min incubations (FIG. 12). Without enhancers, the 12 cm sensors produced very low signals. With the NGPR, a half sensor size, and a half assay time, 4 and 2.5 times of fluorescence enhancements were exhibited for the cTnI and BNP sensing, respectively, accurately quantifying cTnI and BNP.

Thus, fluorescence can be enhanced by well-designed nanogold particles-self-assembled monolayers, possibly by reducing self-quencing of fluorescence via the strong surface plasmon polaritron fields on the surface of a nanogold particle. This enhancement appears to be dependent on the nanogold particle size, the distance between a fluorophore and a nanogold particle, and the QY of a fluorophore. Some organic solvents also enhance the fluorescence significantly. Some biocompatible solvents, e.g. ethanol, are proven to be an optimal, fluorescence enhancer without affecting the reusability of biosensors. To maximize the enhancement effects NGPRs were developed by combining the nanogold particle-self assembled monolayer and the solvent. Among the NGPRs tested, the 5 nm nanogold particles-self-assembled monolayers at a thickness of 2 nm in ethanol was found to be the best enhancer. The mixture demonstrated an enhancement additive by the nanogold particle-self assembled monolayer and by the solvent. By utilizing NGPRs, accurate quantifications of cardiac markers at tens of picomolar level were achieved, enabling real-time heart attack diagnosis.

While specific embodiments of the present invention have been shown and described, it should be understood that other modifications, substitutions and alternatives are apparent to one of ordinary skill in the art. Such modifications, substitutions and alternatives can be made without departing from the spirit and scope of the invention.

The invention claimed is:

1. A method of ascertaining the presence, absence and/or quantification of a target analyte by enhancing fluorescence emission in a fluorophore-mediated sensing application, comprising:

immobilizing a monoclonal antibody with an affinity for a target analyte on a portion of an optical fiber;

placing the portion of the optical fiber in a chamber;

injecting sample suspected to include target analyte into the chamber;

removing unbound molecules from the portion of the optical fiber;

probing the portion of the optical fiber with a second monoclonal antibody tagged with a fluorophore in the chamber;

exposing the portion of the optical fiber to nanometal particles surrounded by a coating having a predetermined thickness, the coating providing a spacer between the nanometal particles and the fluorophore sufficient to prevent fluorescence quenching, wherein said step of exposing provides the nanometal particles in the chamber in a solution that comprises an organic solvent;

sending excitation light into the optical fiber;

sensing responsive fluorescence emissions through the optical fiber; and ascertaining the presence, absence and/or quantification of target analyte from the responsive fluorescence emissions.

2. The method of claim 1 wherein the layer is selected to be one of the group consisting of a self-assembled monolayer, a surfactant and a peptide.

3. The method of claim 1 wherein the nanometal particles are selected to be between approximately 2-100 nm.

4. The method of claim 1 wherein the nanometal particles are nanogold particles.

5. The method of claim 1 wherein the solution comprises a plurality of organic solvents.

6. The method of claim 1, wherein the nanometal particles are approximately 5 nm nanometal particles and the coating comprises a self-assembled monolayer having a thickness of approximately 2 nm.

7. The method of claim 1, wherein said step of exposing provides the nanometal particles in the chamber in a buffer solution including an organic, biocompatible solvent selected from the group consisting of ethanol and n-Butanol.

8. The method of claim 1, wherein the optical fiber comprises a quartz fiber and the tip of the optical fiber is polished at 45°.

9. The method of claim 1, wherein the portion of the fiber comprises a tapered portion.

10. The method of claim 7, wherein the nanometal particles are nanogold particles.

* * * * *

UNITED STATES PATENT AND TRADEMARK OFFICE
CERTIFICATE OF CORRECTION

| | | |
|---|---|---|
| PATENT NO. | : 7,883,900 B2 | Page 1 of 1 |
| APPLICATION NO. | : 11/394290 | |
| DATED | : February 8, 2011 | |
| INVENTOR(S) | : Kyung A. Kang | |

It is certified that error appears in the above-identified patent and that said Letters Patent is hereby corrected as shown below:

<u>In the Specification:</u>

Col. 9, line 23  Please delete "verity" and insert --verify-- in its place.

Signed and Sealed this
Ninth Day of August, 2011

David J. Kappos
*Director of the United States Patent and Trademark Office*